United States Patent [19]

Robey et al.

[11] Patent Number: 5,245,036
[45] Date of Patent: Sep. 14, 1993

[54] PROCESS FOR THE PREPARATION OF 4-PHENOXYQUINOLINE COMPOUNDS

[75] Inventors: Roger L. Robey, Greenwood; Charles A. Alt; Carl V. DeAmicis, both of Indianapolis, all of Ind.

[73] Assignee: DowElanco, Indianapolis, Ind.

[21] Appl. No.: 879,488

[22] Filed: May 7, 1992

[51] Int. Cl.$^5$ .......................................... C07D 215/33
[52] U.S. Cl. ...................................................... 546/153
[58] Field of Search ........................................ 546/153

[56] References Cited

FOREIGN PATENT DOCUMENTS 0326330 8/1992 European Pat. Off. .
3340493 9/1983 Fed. Rep. of Germany .
3340493 5/1985 Fed. Rep. of Germany .

OTHER PUBLICATIONS

G. Hofle et al., *Agnew, Chem. Int. Ed. Engl.*, 17, 569 (1978).
F. Schriven, *Chem. Soc. Rev.*, 12, 129 (1983).
S. K. Chaudhary, *Tetrahedron Lett.* No. 2, pp. 95-98 (1979).

*Primary Examiner*—C. Warren Ivy
*Assistant Examiner*—D. Margaret M. Mach
*Attorney, Agent, or Firm*—Craig E. Mixan

[57] ABSTRACT

The coupling of 4-haloquinolines with phenolic nucleophiles is accelerated by performing the reaction in the presence of a catalytic amount of 4-dialkylaminopyridine.

10 Claims, No Drawings

PROCESS FOR THE PREPARATION OF 4-PHENOXYQUINOLINE COMPOUNDS

FIELD OF THE INVENTION

The present invention concerns an improved process for the preparation of substituted 4-phenoxyquinolines by coupling a substituted 4-haloquinoline with a substituted phenol in the presence of a 4-dialkylaminopyridine catalyst.

BACKGROUND OF THE INVENTION

Substituted 4-phenoxyquinolines, such as those

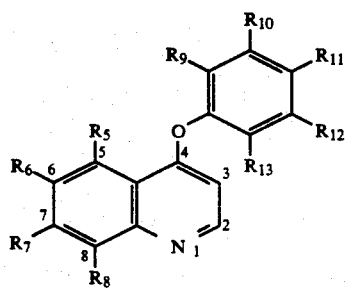

described in EP 326,330, are valuable plant fungicides. Compounds of this type have generally been prepared by condensing a substituted 4-haloquinoline with an excess of a substituted phenol, preferably by refluxing in xylene overnight. Even in refluxing xylene, however, the desired reaction is relatively sluggish, and it would be advantageous to be able to accelerate the rate of the reaction.

SUMMARY OF THE INVENTION

We have now found, that while 4-dialkylaminopyridines are known catalysts for acylation [G. Höfle et al., Angew. Chem. Int. Ed. Engl., 17, 569 (1978) and E. Scriven, Chem. Soc. Rev., 12, 129 (1983)], they also unexpectedly catalyze nucleophilic aromatic substitution reactions at the 4-position of quinolines. Therefore, the present invention concerns a process for the preparation of substituted 4-phenoxyquinolines of formula (I)

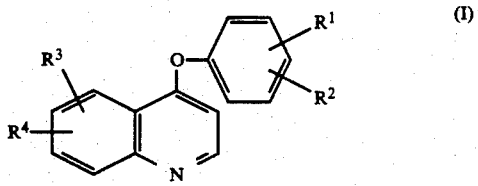

wherein
$R^1$ and $R^2$ independently represent hydrogen, halogen, alkyl or haloalkyl, and
$R^3$ and $R^4$ independently represent hydrogen or halogen,
which comprises reacting a substituted 4-haloquinoline of formula (II)

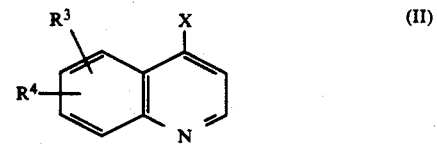

wherein
X represents halogen, and
$R^3$ and $R^4$ are as previously defined,
with a substituted phenol of formula (III)

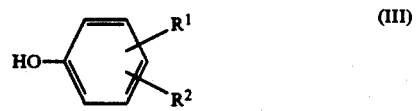

wherein
$R^1$ and $R^2$ are as previously defined,
in the presence of a catalytic amount of a 4-dialkylaminopyridine.

By using a 4-dialkylaminopyridine as a catalyst, batch cycle times are considerably shortened and manufacturing capacity is effectively enlarged.

DETAILED DESCRIPTION OF THE INVENTION

As used herein, the term "alkyl" is meant to designate straight or branched, saturated alkyl groups of from 1 to 4 carbon atoms provided that all substituent groups are sterically compatible with each other. The terms "halo" or "halogen" refer to the members of the group of halogen atoms, i.e., fluorine, chlorine, bromine and iodine. With respect to the present invention, fluorine and chlorine are the preferred halogens. "Haloalkyl" refers to straight or branched, saturated alkyl groups of from 1 to 4 carbon atoms in which the hydrogens have been partially or totally substituted by halogen, again provided that all substituent groups are sterically compatible with each other. The most preferred haloalkyl group is trifluoromethyl.

The term "sterically compatible" is employed to designate substituent groups which are not affected by steric hindrance as this term is defined in *The Condensed Chemical Dictionary*, 7th edition, Reinhold Publishing Co., N.Y. page 893 (1966) which definition is as follows: "steric hindrance: A characteristic of molecular structure in which the molecules have a spatial arrangement of their atoms such that a given reaction with another molecule is prevented or retarded in rate".

Sterically compatible may be further defined as reacting compounds having substituents whose physical bulk does not require confinement within volumes insufficient for the exercise of their normal behavior as discussed in *Organic Chemistry* of D. J. Cram and G. Hammond, 2nd edition, McGraw-Hill book Company, N.Y., page 215 (1964).

The substituted 4-haloquinoline starting materials are known compounds or may be prepared as described in EP 326,330 and the references cited therein. Preferred starting materials of formula (II) are those in which X is chloro and $R^3$ and $R^4$ are independently hydrogen or chloro. $R^3$ and $R^4$ are preferably located in the 5- and/or 7-positions of the quinoline ring system.

The substituted phenol compounds are also known compounds and may be prepared by methods wellknown to those skilled in the art. With respect to the phenolics of formula (III), preferred compounds are those in which $R^1$ and $R^2$ are independently hydrogen, fluoro, chloro or trifluoromethyl. $R^1$ and $R^2$ are preferably located in the 2- and/or 4-positions of the phenol ring.

The 4-dialkylaminopyridine catalysts are also known compounds and can be prepared as described in *Angew. Chem. Int. Ed. Engl.*, 17, 570 (1978) and in *Chem. Soc. Rev.*, 12, 130 (1983). Representative 4-dialkylaminopyridine catalysts include 4-dimethylaminopyridine and 4-pyrrolidinopyridine. In addition, the 4-dialkylaminopyridine can be affixed to a polymer backbone such as polyDMAP TM, a 4-aminopyridine attached to a crosslinked polymer resin, e.g., polystyrene. PolyDMAP TM is a trademark of Reilly Industries, Inc., Indianapolis, Ind. 4-Dimethylaminopyridine is the most preferred catalyst.

In the present invention, the 4-haloquinoline is contacted with the phenol in the presence of a catalytic amount of 4-dialkylaminopyridine. In theory, one equivalent of phenol is required for each equivalent of 4-haloquinoline. In practice, an excess of the phenol is preferred. Generally, from 1 to 2 equivalents of substituted phenol are employed, while from 1.1 to 1.5 equivalents are preferred.

Although the reaction rate is dependent on the concentration of 4-dialkylaminopyridine present, the use of only from about 0.01 to about 0.25 equivalents of 4-dialkylaminopyridine per equivalent of 4-haloquinoline is preferred.

The reaction is usually conducted in an inert organic solvent. Suitable solvents include aromatic hydrocarbons such as, for example, toluene or the xylenes: halogenated hydrocarbons such as, for example, perchloroethylene or chlorobenzene; and polar aprotic solvents such as, for example, dimethylsulfoxide or acetonitrile.

The present reaction is conducted at elevated temperatures of from about 70° to about 175° C. Often, it is most convenient to run the reaction at the reflux temperature of the solvent. Pressures are not critical; and, while the reaction can be conducted at superatmospheric pressure, operation at atmospheric pressure is often most convenient.

In carrying out the present reaction, the 4-haloquinoline, phenol, solvent and dialkylaminopyridine are introduced into a reactor and heated at reflux until the reaction is essentially complete, usually in from 12 to 24 hours, depending upon the particular reagents employed. After completion of the reaction, the desired 4-phenoxyquinoline can be isolated by conventional techniques such as precipitation/crystallization or pH controlled extraction.

The following examples illustrate the practice of the invention and should not be construed as limiting. Melting points are uncorrected.

EXAMPLE 1

Preparation of 4-(2-Trifluoromethylphenoxy)-7-chloroquinoline

To a 50 milliliter (mL) flask equipped with a condenser, drying tube and thermometer was added 1.98 grams (g) (0.01 moles) of 4,7-dichloroquinoline, 2.27 g (0.014 moles) of 2-trifluoromethylphenol, 0.18 g (0.0015 moles) of 4-dimethylaminopyridine (4-DMAP) and 20 mL of xylene. The reaction mixture was heated to reflux (~139° C.) and reaction progress was monitored by thin layer chromatography (TLC). After 24 hours (hr), the 4,7-dichloroquinoline had been completely converted and the reaction mixture was cooled to room temperature and diluted with an additional 20 mL of xylene. Anhydrous HCl was bubbled into the reaction mixture for 5 minutes (min) and the reaction mixture was cooled to 0° C. The hydrochloride salt of the product was collected by filtration, washed with ethyl acetate and dried to give 3.37 g of crystalline solid, mp=210°–215° C. The hydrochloride salt was suspended in 20 mL of water and the pH was adjusted to 7 with 1N NaOH. The 4-(2-trifluoro-methylphenoxy)-7-chloroquinoline was isolated by filtration and was dried under vacuum. Yield: 2.87 g (89 percent), mp 65°–67° C. $^1$H NMR (CDCl$_3$): δ 6.66 (d, 1H), 7.24 (d, 1H), 7.39 (t, 1H), 7.50 (dd, 1H), 7.58 (t, 1H), 7.71 (d, 1H), 7.96 (d, 1H), 8.11 (d, 1H), and 8.46 (d, 1H).

EXAMPLE 2

Preparation of 4-(4-Fluorophenoxy)-7-chloroquinoline

To a 50 mL flask equipped with a condenser, drying tube and thermometer, was added 1.98 g (0.01 moles) of 4,7-dichloroquinoline, 1.57 g (0.014 moles) of 4-fluorophenol, 0.18 g (0.0015 moles) of 4-DMAP and 20 mL of xylene. The reaction mixture was heated to reflux (~140° C.) and reaction progress was monitored by TLC. After 18.5 hr, the reaction was complete and the mixture was cooled to room temperature and diluted with an additional 20 mL of xylene. Anhydrous HCl was bubbled into the reaction mixture for 5 min and the reaction mixture was cooled to 0° C. The hydrochloride salt of the product was collected by filtration, washed with ethyl acetate and dried to give 2.98 g of crystalline solid, mp=203–215° C. The hydrochloride salt was suspended in 20 mL of water and the pH was adjusted to 7 with 1N NaOH. The 4-(4-fluorophenoxy)-7-chloroquinoline was isolated by filtration and was dried under vacuum. Yield: 2.39 g (87 percent), mp=89°–91° C. $^1$H NMR (CDCl$_3$): δ6.45 (t, 1H), 7.15 (m, 4H), 7.5 (dd, 1H), 8.07 (d, 1H), 8.3 (dd, 1H) and 8.65 (t, 1H).

EXAMPLE 3

Preparation of 4-(4-Fluorophenoxy)-7-chloroquinoline

To a 50 mL flask equipped with a condenser, drying tube and thermometer, was added 1.98 g (0.01 moles) of 4,7-dichloroquinoline, 1.07 g (0.0015 moles) of polyDMAP TM and 20 mL of xylene. The mixture was stirred to reswell the polymer and 1.57 g (0.0014 moles) of 4-fluorophenol were added. The reaction mixure was heated to reflux and maintained at that temperature for 18 hr. The reaction mixture was filtered hot to remove the polymer. After cooling, the filtrate was washed with 50 mL of 5N NaOH. The caustic layer was extracted with 2×25 mL of diethyl ether. The xylene and the ether layers were combined and dried over Na$_2$SO$_4$. Removal of the solvent provided 2.36 g (86 percent yield) of product, mp=89°–91° C.

EXAMPLE 4

Preparation of 4-(4-Fluorophenoxy)-7-chloroquinoline

To a 50 mL flask equipped with a condenser, drying tube and thermometer, was added 1.98 g (0.01 moles) of 4,7-dichloroquinoline, 1.57 g (0.0014 moles) of 4-fluorophenol, 0.22 g (0.0015 moles) of 4-pyrrolidinopyridine and 20 mL of xylene. The reaction mixture was heated to reflux and reaction progress was monitored by TLC. After 18 hr, the mixture was cooled and washed with 50 mL of 5 N NaOH. The caustic layer was extracted with 3×20 mL of diethyl ether. The xylene and the ether layers were combined and dried over Na$_2$SO$_4$. Removal of the solvent provided 2.49 g (91 percent yield) of product, mp=88°–91° C.

EXAMPLE 5

Preparation of 4-(4-Fluorophenoxy)-5,7-dichloroquinoline

To a 50 mL flask equipped with a condenser, drying tube and thermometer, was added 2.33 g (0.01 moles) of 4,5,7-trichloroquinoline, 1.57 g (0.014 moles) of 4-fluorophenol, 0.18 g (0.0015 moles) of 4-DMAP and 20 mL of xylene. The reaction mixture was heated to reflux (~140° C.) and reaction progress was monitored by TLC. After 16 hr, the reaction was complete and the mixture was cooled to room temperature and diluted with an additional 20 mL of xylene. Anhydrous HCl was bubbled into the reaction mixture for 5 min and the reaction mixture was cooled to 0° C. The hydrochloride salt of the product was collected by filtration, washed with ethyl acetate and dried to give 3.46 g of crystalline solid, mp=207°–222° C. The hydrochloride salt was suspended in 20 mL of water and the pH was adjusted to 7 with 1N NaOH. The 4-(4-fluorophenoxy)-5,7-dichloroquinoline was isolated by filtration and was dried under vacuum. Yield 2.86 g (93 percent), mp=94°–97° C. $^1$H NMR (CDCl$_3$): δ6.6 (d, 1H), 7.15 (m, 4H), 7.6 (d, 1H), 8.05 (d, 1H) and 8.65 (d, 1H).

What is claimed is:

1. A process for the preparation of substituted 4-phenoxyquinolines of formula (I)

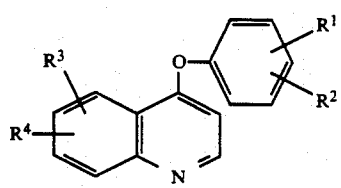

wherein

R$^1$ and R$^2$ independently represent hydrogen, halogen, alkyl or haloalkyl, and R$^3$ and R$^4$ independently represent hydrogen or halogen, which consists essentially of reacting a substituted 4-haloquinoline of formula (II)

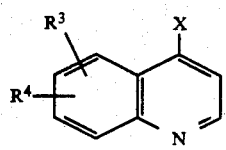

wherein

X represents halogen, and

R$^3$ and R$^4$ are as previously defined, with a substituted phenol of formula (III)

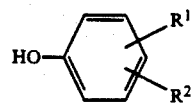

wherein

R$^1$ and R$^2$ are as previously defined, in the presence of a catalytic amount of a 4-dialkylaminopyridine.

2. The process of claim 1 in which the 4-dialkylaminopyridine is 4-dimethylaminopyridine or 4-pyrrolidinopyridine.

3. The process of claim 1 in which the 4-dialkylaminopyridine is a 4-aminopyridine attached to a crosslinked polymer resin.

4. The process of claim 1 in which X is chloro and R$^3$ and R$^4$ are independently hydrogen or chloro.

5. The process of claim 4 in which R$^3$ and R$^4$ are located at the 5- and/or 7-position of the quinoline ring.

6. The process of claim 1 in which R$^1$ and R$^2$ are independently hydrogen, fluoro, chloro or trifluoromethyl.

7. The process of claim 6 in which R$^1$ and R$^2$ are located at the 2- and/or 4-position of the phenol ring.

8. A process for the preparation of substituted 4-phenoxyquinolines of formula (I)

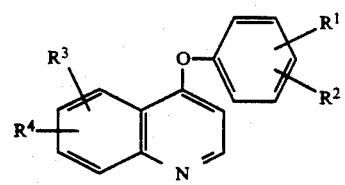

wherein

R$^1$ and R$^2$ independently represent hydrogen, fluoro, chloro or trifluoromethyl, and R$^3$ and R$^4$ independently represent hydrogen and chloro, which consists essentially of reacting a substituted 4-chloroquinoline of formula (II)

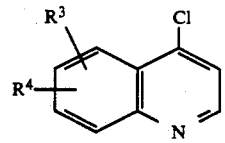

wherein

R$^3$ and R$^4$ are as previously defined, with a substituted phenol of formula (III)

wherein

R$^1$ and R$^2$ are as previously defined, in the presence of a catalytic amount of 4-dimethylaminopyridine.

9. The process of claim 8 in which R$^3$ and R$^4$ are located at the 5- and/or 7-position of the quinoline ring.

10. The process of claim 8 in which R$^1$ and R$^2$ are located at the 2- and/or 4-position of the phenol ring.

* * * * *